US012115089B2

(12) United States Patent
Castelli

(10) Patent No.: US 12,115,089 B2
(45) Date of Patent: Oct. 15, 2024

(54) CLAMSHELL IRIS-STYLE CRIMPER FOR MEDICAL DEVICES

(71) Applicant: MEDTRONIC, INC., Minneapolis, MN (US)

(72) Inventor: Brian Castelli, Santa Rosa, CA (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

(21) Appl. No.: 17/909,810

(22) PCT Filed: Mar. 22, 2021

(86) PCT No.: PCT/US2021/023500
§ 371 (c)(1),
(2) Date: Sep. 7, 2022

(87) PCT Pub. No.: WO2021/194976
PCT Pub. Date: Sep. 30, 2021

(65) Prior Publication Data
US 2023/0128718 A1 Apr. 27, 2023

Related U.S. Application Data

(60) Provisional application No. 63/000,079, filed on Mar. 26, 2020.

(51) Int. Cl.
*A61F 2/95* (2013.01)
*A61F 2/24* (2006.01)

(52) U.S. Cl.
CPC .......... *A61F 2/9524* (2020.05); *A61F 2/2433* (2013.01)

(58) Field of Classification Search
CPC .............................. A61F 2/9524; A61F 2/2433
See application file for complete search history.

(56) References Cited

U.S. PATENT DOCUMENTS

| 5,261,263 A | 11/1993 | Whitesell |
| 5,893,867 A | 4/1999 | Bagaoisan et al. |

(Continued)

FOREIGN PATENT DOCUMENTS

| WO | 0121076 A1 | 3/2001 |
| WO | 2015179181 A1 | 11/2015 |

(Continued)

OTHER PUBLICATIONS

International Search Report issued Jun. 12, 2021 in Intl Appl. No. PCT/US2021/023500.

*Primary Examiner* — Ryan J. Walters
(74) *Attorney, Agent, or Firm* — MEDLER FERRO WOODHOUSE & MILLS PLLC

(57) ABSTRACT

A crimper includes atop iris shell defining atop iris channel. The crimper also includes abase iris shell coupled to the top iris shell at a pivot connection, the base iris shell defining a base iris channel. The top iris shell is configured to rotate about the pivot connection relative to the base shell from an open state to a closed state. When in the open state, the base iris channel is exposed for loading the expandable medical device. When in the closed state, the top iris channel and the base iris channel define a crimper chamber. The crimper also includes a handle configured to operate the clamshell crimper. The actuation of the handle decreases a volume of the crimper chamber to transition the expandable medical device from the uncompressed state to the compressed state.

18 Claims, 15 Drawing Sheets

(56) References Cited

U.S. PATENT DOCUMENTS

| | | | |
|---|---|---|---|
| 6,309,383 B1 | 10/2001 | Campbell et al. | |
| 6,889,579 B1 | 5/2005 | Brown | |
| 7,225,518 B2 | 6/2007 | Eidenschink et al. | |
| 7,530,253 B2 | 5/2009 | Spenser et al. | |
| 7,628,051 B1 * | 12/2009 | Kokish | A61F 2/9524 |
| | | | 72/402 |
| 7,886,569 B2 | 2/2011 | Weber et al. | |
| 8,006,535 B2 | 8/2011 | Righini | |
| 8,099,851 B2 | 1/2012 | Roach et al. | |
| 8,104,321 B2 | 1/2012 | Serrano et al. | |
| 8,151,445 B1 | 4/2012 | Warriner et al. | |
| 8,533,925 B2 | 9/2013 | Austin | |
| 8,539,663 B2 | 9/2013 | Wang et al. | |
| 8,833,209 B2 | 9/2014 | Brown | |
| 9,757,232 B2 | 9/2017 | Peterson et al. | |
| 10,568,697 B2 | 2/2020 | Baldauf et al. | |
| 10,716,691 B2 | 7/2020 | Saar | |
| 11,052,521 B2 | 7/2021 | Van Breda | |
| 11,844,713 B2 * | 12/2023 | Castelli | A61F 2/9524 |
| 2002/0138966 A1 | 10/2002 | Motsenbocker | |
| 2005/0183259 A1 | 8/2005 | Eidenschink et al. | |
| 2011/0257673 A1 | 10/2011 | Heraty et al. | |
| 2013/0178928 A1 | 7/2013 | Vyas et al. | |
| 2013/0218139 A1 | 8/2013 | Fargahi | |
| 2016/0270914 A1 | 9/2016 | Krans et al. | |
| 2018/0344490 A1 | 12/2018 | Fox et al. | |
| 2019/0201225 A1 | 7/2019 | Sirhan et al. | |
| 2021/0030533 A1 | 2/2021 | Tamir | |
| 2022/0039979 A1 * | 2/2022 | Castelli | A61F 2/9524 |
| 2024/0041624 A1 * | 2/2024 | Mitchell | A61F 2/9524 |

FOREIGN PATENT DOCUMENTS

| | | |
|---|---|---|
| WO | 2017031412 A1 | 11/2015 |
| WO | 2017139421 A1 | 8/2017 |
| WO | 2019212812 A1 | 11/2019 |
| WO | 2021194976 A1 | 9/2021 |

* cited by examiner

CLAMSHELL IRIS-STYLE CRIMPER FOR MEDICAL DEVICES

FIELD

The present technology is generally related to medical devices. And, more particularly, to devices for crimping stents, prosthetic heart valves and other implantable vascular medical appliances.

BACKGROUND

Currently, expandable implantable medical devices that include a stent structure and organic tissue, e.g., bovine and porcine, such as prosthetic valves and other cardiac intervention devices, require onsite crimping onto a delivery device at the implantation site, e.g., a catheterization laboratory ("cath lab"). This is due to the need to store the implantable devices in conditions specific to preserve the organic tissue. Typically, aftermarket iris-style crimpers are utilized in the crimping processes. Current iris-style crimpers experience limitations due to side loading that leads to the difficulty in accurately placing medical devices relative to the delivery device inside of side loading crimpers. With tissue containing implantable devices that need to be crimped by medical personnel immediately before implantation, this difficulty can lead to time delays and more damage to the devices by operators not experienced in the processes for crimping the medical device. Given the cost of such devices, the possibility of destroying or damaging such devices can be significant.

SUMMARY

The techniques of this disclosure generally relate to a clamshell crimper for loading an implantable medical device onto a delivery device and converting the implantable medical device from an expanded state to a compressed state. The clamshell crimper is designed to allow top loading of the implantable medical device for improved alignment with the crimper and the delivery device. The clamshell crimper provides a solution for compressing and loading implantable medical devices at a location (e.g., hospital, surgical facility, etc.) where the medical devices will be implanted. Further, the open, top loading design of the clamshell crimper provides increased visibility in loading and aligning the implantable medical devices and the delivery device as well as rapid fine adjustments. Additionally, the clamshell crimper provides a straightforward design which reduces manufacturing and replacement cost.

In one aspect, the present disclosure provides a clamshell crimper for altering an expandable medical device from an uncompressed state to a compressed state. The crimper includes a top shell comprising a first plurality of lobes, the first plurality of lobes defining a top channel The crimper also includes a base shell comprising a second plurality of lobes, the second plurality of lobes defining a bottom channel The top shell and the base shell are coupled at a pivot connection. The top shell is configured to rotate about the pivot connection relative to the base shell from an open state to a closed state. When in the open state, the second channel is exposed for loading the expandable medical device. When in the closed state, the top channel and the bottom channel define a crimper chamber. The crimper also includes a handle configured to operate the clamshell crimper. Further, the crimper includes one or more actuator rings coupled to the handle, the first plurality of lobes, and the second plurality of lobes. When in the closed state, movement of the handle rotates the one or more actuator rings thereby displacing the first plurality of lobes and the second plurality of lobes. The displacement of the first plurality of lobes and the second plurality of lobes decreases a volume of the crimper chamber to transition the expandable medical device from the uncompressed state to the compressed state.

In another aspect, the present disclosure provides a clamshell crimper for altering an expandable medical device from an uncompressed state to a compressed state. The crimper includes a top iris shell defining a top iris channel The crimper also includes a base iris shell coupled to the top iris shell at a pivot connection, the base iris shell defining a base iris channel The top iris shell is configured to rotate about the pivot connection relative to the base shell from an open state to a closed state. When in the open state, the base iris channel is exposed for loading the expandable medical device. When in the closed state, the top iris channel and the base iris channel define a crimper chamber. The crimper also includes a handle configured to operate the clamshell crimper. The actuation of the handle decreases a volume of the crimper chamber to transition the expandable medical device from the uncompressed state to the compressed state.

In another aspect, the present disclosure provides a method for altering an expandable medical device from an uncompressed state to a compressed state. The method includes placing a clamshell crimper in an open state, where the clamshell crimper includes a top iris shell and a base iris shell connected by a pivot connection. When in the open state, a base iris channel of the base iris shell is exposed for loading the expandable medical device. The method also includes loading the expandable medical device into the iris channel of the base iris shell. Further, the method includes transitioning the crimper from the open state to a closed state. When in the closed state, a top iris channel of the top iris shell and the base iris channel of the base iris shell define a crimper chamber. Additionally, the method includes actuating a handle of the clamshell crimper. The actuation of the handle decreases a volume of the crimper chamber to transition the expandable medical device from the uncompressed state to the compressed state.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

DETAILED DESCRIPTION

Specific embodiments of the present disclosure are now described with reference to the figures. The following detailed description describes examples of embodiments and is not intended to limit the present technology or the application and uses of the present technology. Although the description of embodiments hereof is in the context of a crimper, the present technology may also be used in other devices. Furthermore, there is no intention to be bound by any expressed or implied theory presented in the preceding technical field, background, brief summary or the following detailed description.

Embodiments disclosed herein are directed to a clamshell crimper for loading an implantable medical device onto a delivery device and converting the implantable medical device from an expanded state to a compressed state. In embodiments, the clamshell crimper includes a top iris shell and a base iris shell. The top iris shell can be rotated away from the base iris shell to expose a channel for loading and positioning the implantable medical device and the delivery device. When closed, the channel of the base iris shell and a corresponding channel in the top iris shell form a crimper chamber around the expandable medical device. The clamshell crimper can then be actuated to decrease the volume of the crimper chamber though the process of iris-style displacement of lobes.

Figure 1A:
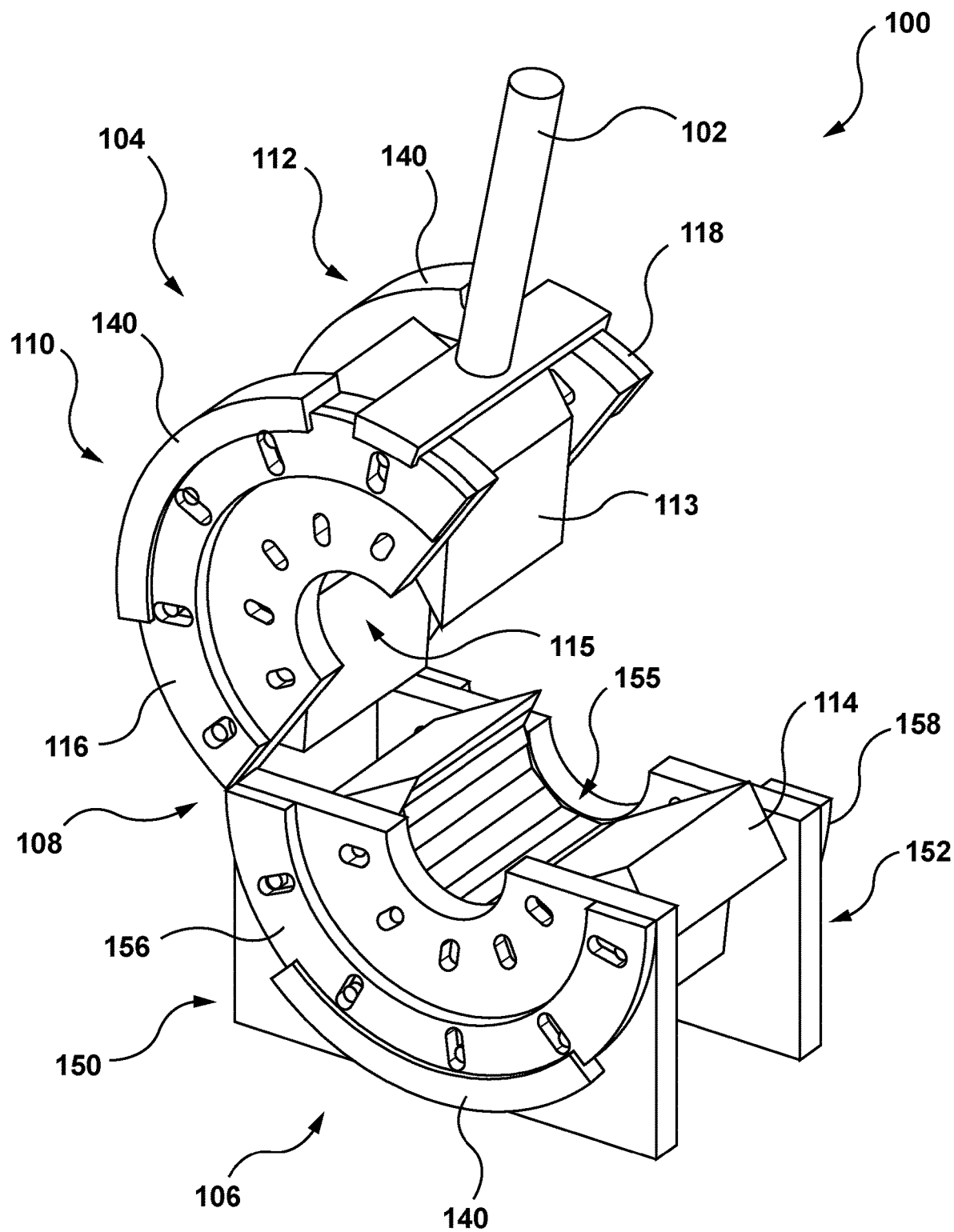
FIGS. 1A-1C depict different perspective illustrations of a clamshell crimper for use with a medical device, according to an embodiment hereof.
Figure 1B:
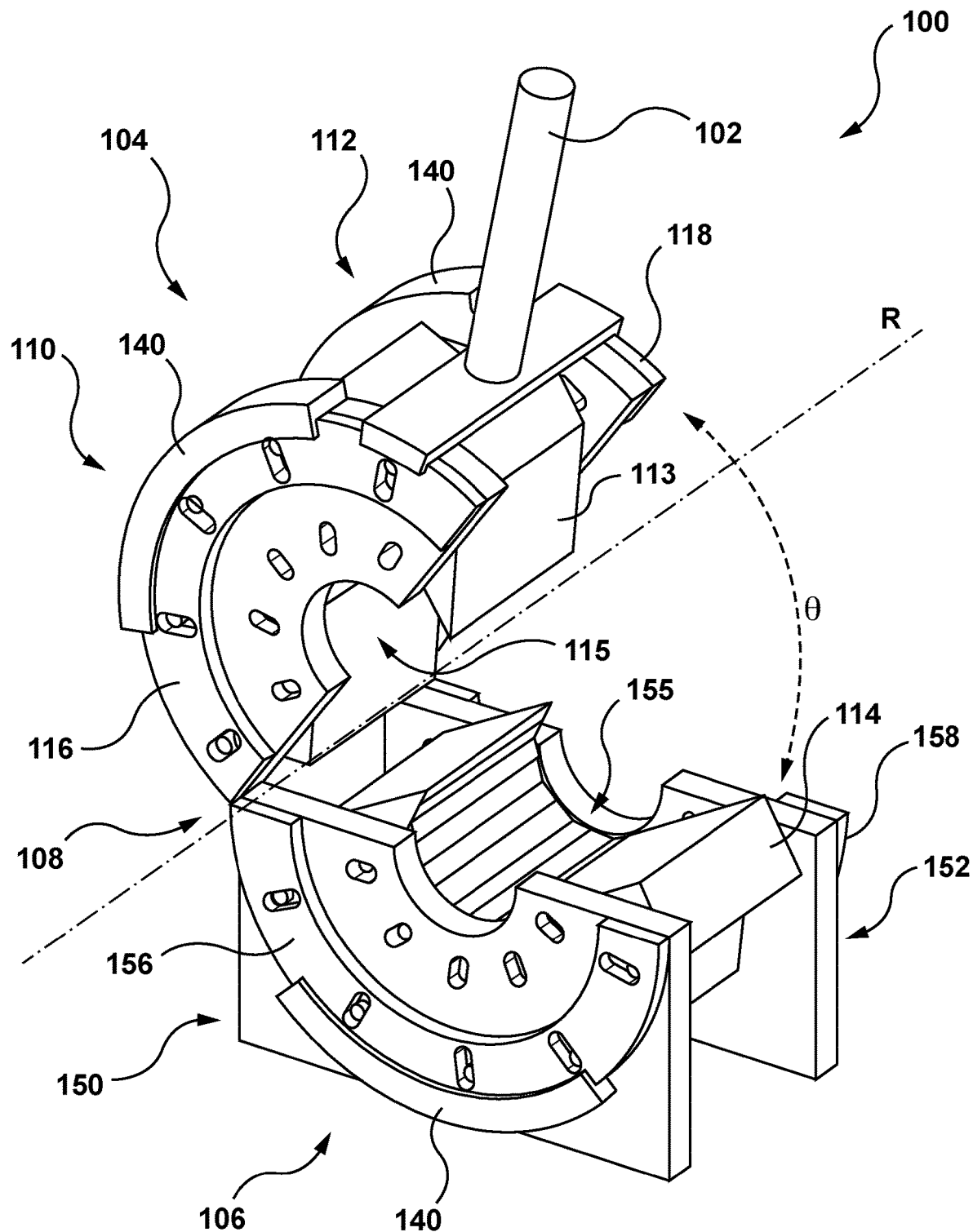
Figure 1C:
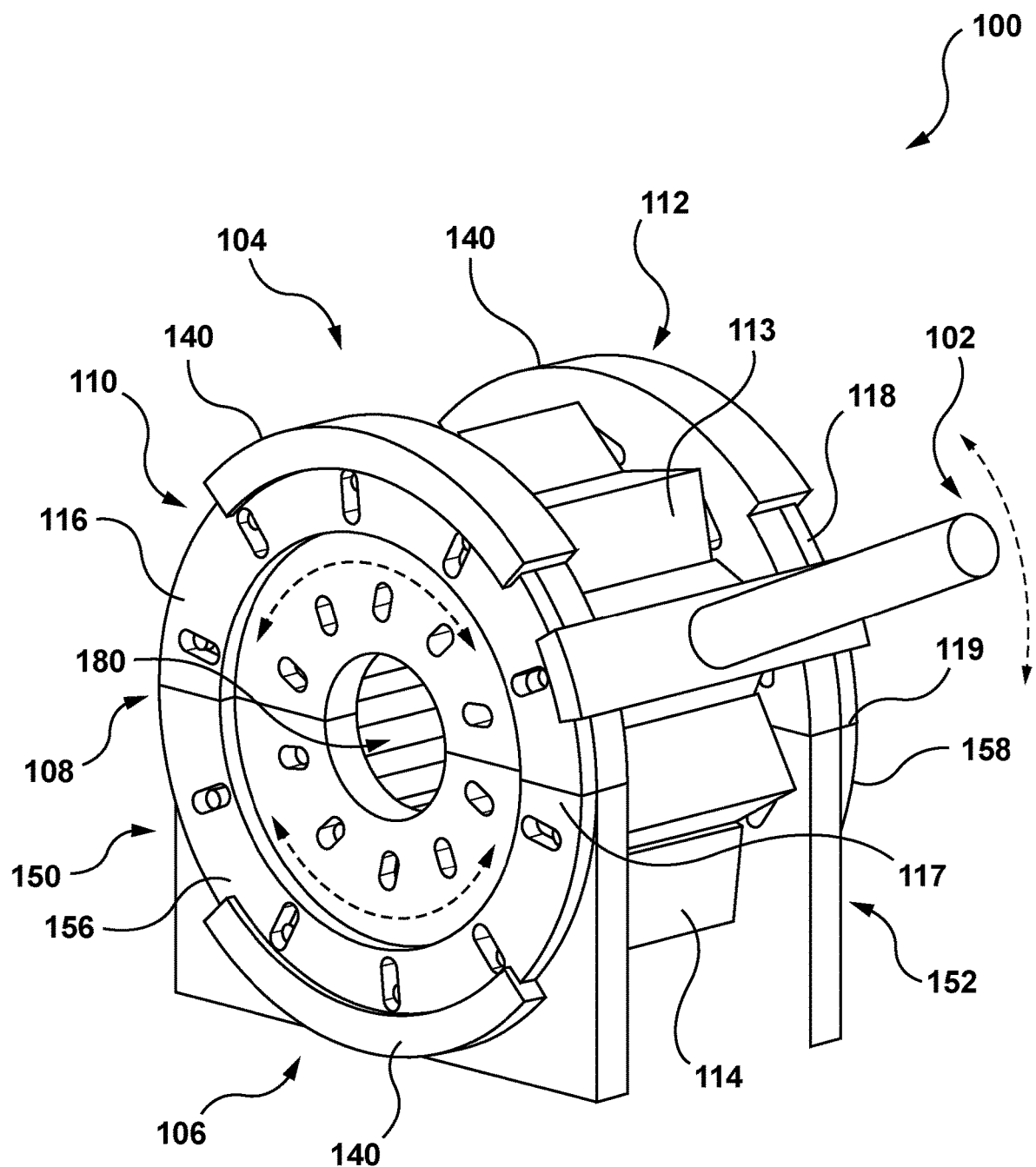

FIGS. 1A-1C illustrate an example of a clamshell crimper 100 in accordance with an embodiment hereof. One skilled in the art will realize that FIGS. 1A-1C illustrate one example of a crimper and that existing components illustrated in FIGS. 1A-1C may be removed and/or additional components may be added to the clamshell crimper 100.

As illustrated in FIG. 1A, the clamshell crimper 100 includes a handle 102, a top shell 104 (or top iris shell), and a base shell 106 (or base iris shell). The top shell 104 and the base shell 106 are coupled at a pivot connection 108. In an embodiment, the pivot connection 108 can include a pin that is positioned corresponding circular openings in the top shell 104 and the base shell 106. For example, the pin can be a dowel pin, a bolt, and the like. The pin can be formed to a diameter to maintain the corresponding circular openings and cause the pin to operate as a fulcrum. In an embodiment, the top shell 104 and the base shell 106 can be separate components that can be removably attached at the pivot connection 108 to form the clamshell crimper 100. In another embodiment, the top shell 104 and the base shell 106 can be a single component that fold towards each other, for instance, via a living hinge therebetween, to form an integrated clamshell crimper 100. The top shell 104 and the base shell 106 can be formed of any suitable material such as, but not limited to aluminum, stainless steel, or a polymeric material. While the clamshell crimper 100 is described as pivoting at the pivot connection 108, one skilled in the art will realize that top shell 104 and the base shell 106 can move relative to one another using other type of processes and mechanically connections.

As illustrated in FIG. 1B, the pivot connection 108 allows an angle, θ, between the top shell 104 and the base shell 106 to be increased or decreased by rotating the top shell 104 away from the base shell about an axis of rotation, R. The pivot connection 108 is configured to allow the top shell 104 and the base shell 106 to move relative to each other from an open state (illustrated in FIG. 1B) to a closed state (illustrated in FIG. 1C) and discussed in detail below with reference to FIGS. 3A-3E. As described herein, an open state for the clamshell crimper 100 defines any angle, θ, between the top shell 104 and the base shell 106 that allows a user to insert an implantable medical device and/or delivery device in the clamshell crimper 100 and that allows a user to view the insertion to properly align the implantable medical device and the delivery device. As described herein, the closed state defines any angle, θ, between the top shell 104 and the base shell 106 in which the clamshell crimper 100 is operating to compress the implantable medical device and to crimp or load the implantable medical device onto a delivery device. For example, in an embodiment, the angle, θ, between the top shell 104 and the base shell 106, when in the open state, can range from approximately 45 degrees to approximately 180 degrees. Likewise, for example, in an embodiment, the angle, θ, between the top shell 104 and the base shell 106, when in closed state, can be approximately 0 degrees.

The pivot connection 108 can be any type of mechanical joint or electro-mechanical joint that allows the top shell 104 and the base shell 106 to move relative to each other. For example, the pivot connection 108 can include one or more of a hinge, a rivet, a pivot pin, a pivot joint, an axle, a living hinge, etc. In an embodiment, the pivot connection 108 can include a movement assistance device to provide a force that assists in the movement of the top shell 104 and the base shell 106 relative to each other. For example, the pivot connection 108 can include a spring, a motor, etc. In some embodiments, the top shell 104 and the bottom shell 106 can include tabs that extend from back of the top shell 104 and the bottom shell 106. The tabs, when mated, can form a concentric hole that operates as the pivot connection 108 when pin, rivet, bolt, screw or other connecting mechanism.

Returning to FIG. 1A, the top shell 104 includes a first side 110 and a second side 112. A plurality of lobes 113 are coupled between the first side 110 and the second side 112. The plurality of lobes 113 are positioned to partially overlap within the top shell 104 to define atop channel 115. The first side 110 of the top shell 104 also includes atop portion 116 of an actuator ring 117. The second side 112 of the top shell 104 also includes a top portion 118 of an actuator ring 119.

The base shell 106 includes a first side 150 and a second side 152. A plurality of lobes 114 are coupled between the first side 150 and the second side 152. The plurality of lobes 114 are positioned to partially overlap within the base shell 106 to define a bottom channel 155. The first side 150 of the base shell 106 also includes a bottom portion 156 of the actuator ring 117. The second side 152 of the base shell 106 also include a bottom portion 158 of the actuator ring 119.

The plurality of lobes 113 and 114 are arranged to partially overlap between the top shell 104 and the base shell 106, respectively, in a first direction. In an embodiment, the lobes 113 of the top shell 104 are arranged to partially overlap to form the top channel 115 at distal ends of the lobes 113 (e.g., distal end 177 described below with reference to FIG. 2C). The lobes 114 of the base shell 106 are arranged to partially overlap to form the bottom channel 155 at distal ends of the lobes 114 (e.g., distal end 177 described below with reference to FIG. 2C). When the clamshell crimper 100 is in the closed state, the top channel 115 and the bottom channel 155 define a crimper chamber 180. That is, when in the closed state, the plurality of lobes 113 of the top shell 104 and the plurality of lobes 114 of the base shell 106 form a cylinder of overlapping lobes with a cylindrical-shaped cavity passing through the center, defining the crimper chamber 180.

The handle 102 is coupled the top portion 116 of the actuator ring 117 and the top portion 118 of the actuator ring 119. In some embodiments, the handle 102 can be formed a separate component that is attached to the actuator ring 117 and actuator ring 119. In other embodiments, the handle 102 can be integrated as a one piece handle with the top portion 116 of the actuator ring 117 and the top portion 118 of the actuator ring 119.

In embodiments, the top shell 104 can include a lock mechanism that locks the handle 102 into an open position, e.g., the crimper chamber 180 in an open position. The top shell 104 and/or the bottom shell 106 can include a locking mechanism that locks the top shell 104 and the bottom shell 106 together in a closed state. When the handle 102 is locked, the clamshell crimper 100 can be moved into an open state by pivoting the top shell 104 away from the bottom shell 106. During crimping operations, the top shell 104 can be closed, for example, using the handle 102, and the top shell 104 and the bottom shell 106 can be locked into the closed state. The handle 102 can then be unlocked to perform crimping operations. The dual locking can prevent either the top shell 104 or the bottom shell 106 from moving to the closed position while the other half is in the open position.

In embodiments, the handle 102 can be shape, size, design, and/or configuration to accommodate different crimping operations. For example, the handle 102 can be extended and include a pivot point to add more leverage during crimping operations. Likewise, the handle 102 can include a foot pedal that assists in pulling down the handle 102.

When in the closed state, the lobes 113 and 114 are displaced by the movement of the handle 102. As such, the lobes 113 and 114 function as an iris to decrease or increase the volume of the crimper chamber 180 through the movement of the handle 102, as described below in further detail. As illustrated in FIG. 1C, the crimper chamber 180 can define a volume that approximates a cylinder. While the crimper chamber 180 is described above as defining a cylindrical shaped volume, one skilled in the art will realize that the shape and dimension of the lobes can be changed to create a differently shaped volume as required by the implantable medical device being compressed and positioned.

The clamshell crimper 100 is configured to receive an implantable medical device and alter the implantable medical device from an uncompressed state to a compressed state by the displacement of the lobes 113 and 114, which causes the decrease of the volume of the crimper chamber 180. Additionally, the clamshell crimper 100 is configured to crimp or load the implantable medical device onto a delivery device. In an embodiment, the lobes 113 and 114 can be removable from the top shell 104 and/or base shell 106. As such, the lobes 113 and 114 may be interchangable with other types of lobes configured to accommodate different dimensions and/or configurations of implantable medical devices and/or delivery devices. The lobes 113 and 114 may be formed of any suitable material such as, but not limited to aluminum, stainless steel, or a polymeric material.

Figure 2A:
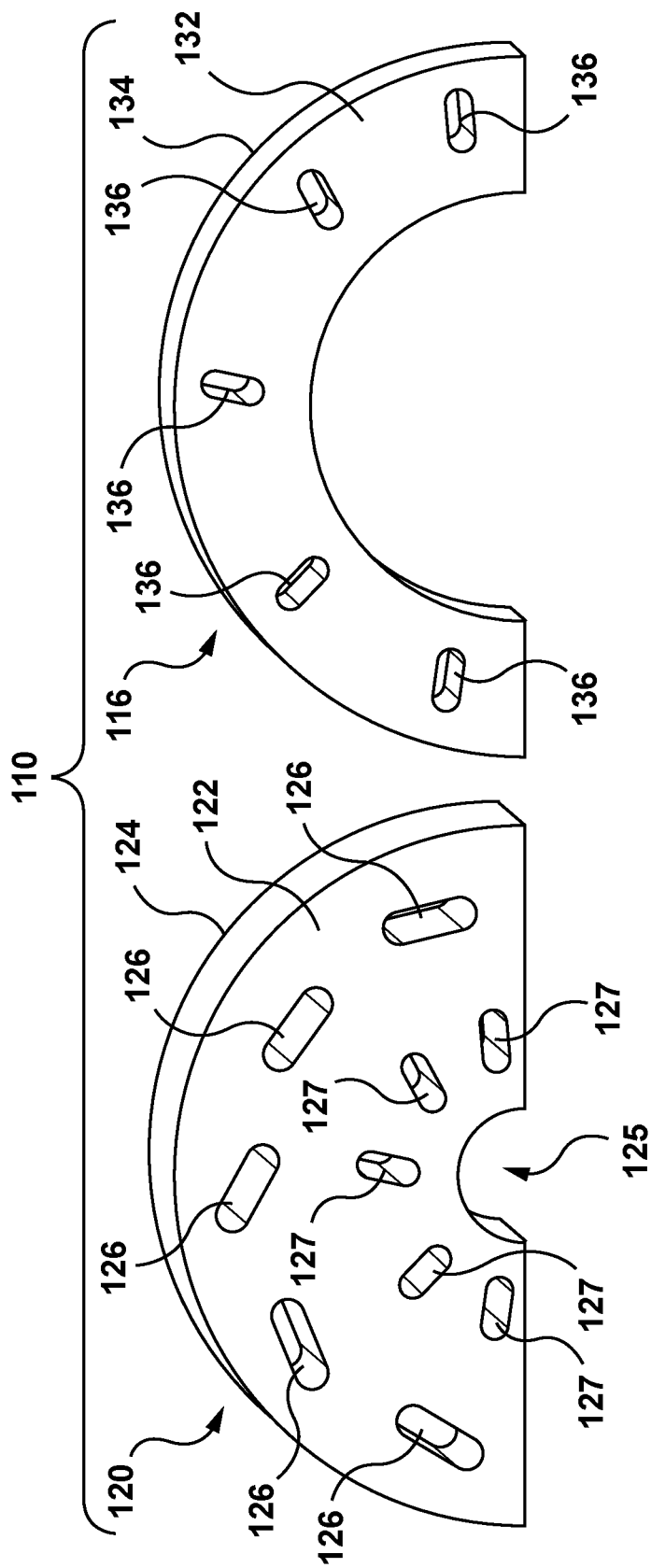
FIG. 2A depicts an exploded perspective illustration of a side of a top shell of the crimper of FIGS. 1A-1C, according to an embodiment hereof.

FIG. 2A illustrates a detailed view of components of the first side 110 of the top shell 104. One skilled in the art will realize that FIG. 2A illustrates one example of a side of the top shell 104 and that existing components illustrated in FIG. 2A may be removed and/or additional components may be added to the first side. Additionally, while the first side 110 is only discussed below, one skilled in the art will realize that second side 112 may include the same components as illustrated in FIG. 2A.

As illustrated in FIG. 2A, the first side 110 includes a side plate 120 with a front surface 122 and a back surface 124. In an embodiment, the side plate 120 can be constructed as a semi-cylindrical plate with a semi-cylindrical opening 125. The semi-cylindrical opening 125 allows access to the top channel 115 formed by the plurality of lobes 113. First connection channels 126 are formed through the side plate 120 from the front surface 122 to the back surface 124. The first connection channels 126 can be positioned in an arc, at equal distances, along an outer edge of the side plate 120. Second connection channels 127 are formed through the side plate 120 from the front surface 122 to the back surface 124. The second connection channels 127 can be positioned in an arc, at equal distances, along an inner edge of the side plate 120 around the opening 125.

The first side 110 also includes the top portion 116 of the actuator ring 117. The top portion 116 of the actuator ring 117 includes a front surface 132 and a back surface 134. The top portion 116 of the actuator 117 can be constructed as a semi-cylindrical ring. When in combination, the top portion 116 and the bottom portion 156 form the actuator ring 117 in a cylindrical ring shape. Third connection channels 136 are formed through the top portion 116 of the actuator ring 117 from the front surface 132 to the back surface 134. The third connection channels 136 can be positioned in an arc, at equal distances, along the top portion 116 of the actuator ring 117. As illustrated in FIG. 1A-1C, the top portion 116 of the actuator ring 117 can be movably positioned on the side plate 120 by a retention member 140.

Figure 2B:
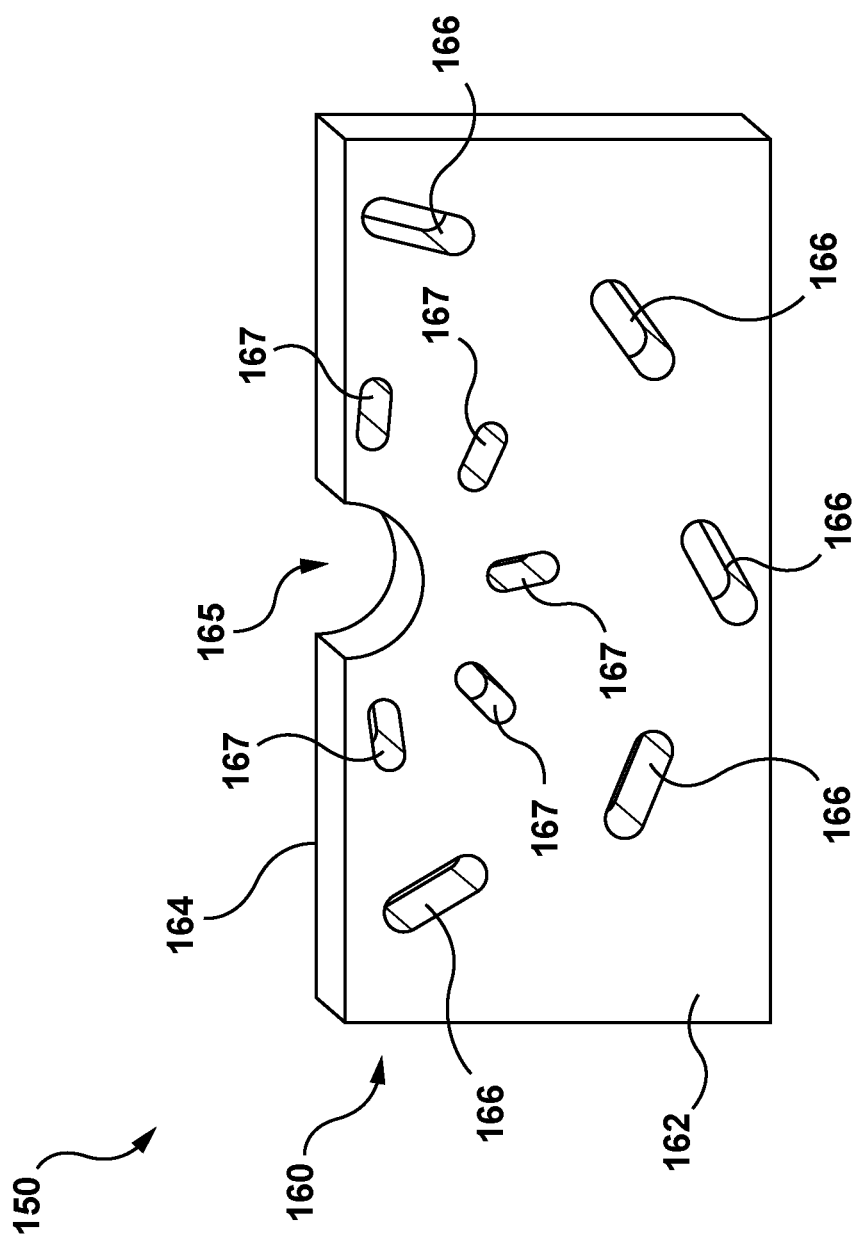
FIG. 2B depicts a perspective illustration of a side of a base shell of the crimper of FIGS. 1A-1C, according to an embodiment hereof.

FIG. 2B illustrates a detailed view of components of the first side 150 of the base shell 106. One skilled in the art will realize that FIG. 2B illustrates one example of a side of the base shell 106 and that existing components illustrated in FIG. 2B may be removed and/or additional components may be added to the first side. Additionally, while the first side 150 is only discussed below, one skilled in the art will realize that second side 152 may include the same components as illustrated in FIG. 2B. Likewise, while the bottom portion 156 of the actuator ring 117 and the bottom portion 158 of the actuator ring 119 are not discussed below, one skilled in the art will realize that the bottom portion 156 of the actuator ring 117 and the bottom portion 158 of the actuator ring 119 may have the same configuration and include the same components as the top portion 116 of the actuator ring 117, described in FIG. 2A.

As illustrated in FIG. 2B, the first side 150 includes a side plate 160 with a front surface 162, a back surface 164, and a base surface 163. In an embodiment, the side plate 160 can be constructed as a rectangular plate with a semi-cylindrical opening 165. The semi-cylindrical opening 165 allows access to the bottom channel 155 formed by the plurality of lobes 114. First connection channels 166 are formed through the side plate 160 from the front surface 162 to the back surface 164. The first connection channels 166 can be positioned in an arc, at equal distances, along an outer edge of the side plate 160. Second connection channels 167 are formed through the side plate 160 from the front surface 162 to the back surface 164. The second connection channels 167 can be positioned in an arc, at equal distances, along an inner edge of the side plate 160 around the semi-cylindrical opening 165.

Figure 2C:
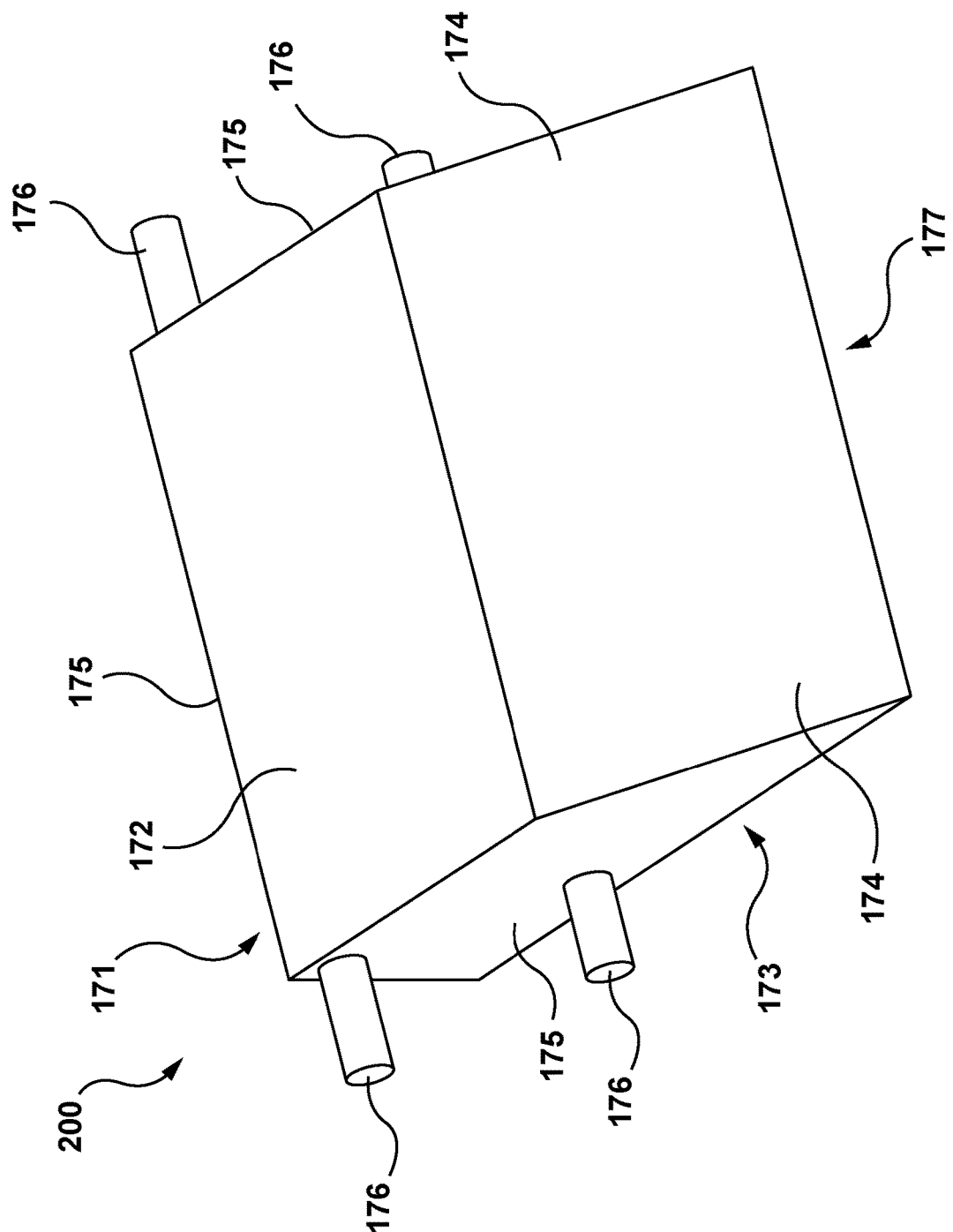
FIG. 2C depicts a perspective illustration of a lobe of the crimper of FIGS. 1A-1C, according to an embodiment hereof.

FIG. 2C illustrates a detailed view of components of one of a lobe 200, which may be used for the lobe 113 and/or the lobe 114. One skilled in the art will realize that FIG. 2C illustrates one example of a lobe and that existing components illustrated in FIG. 2B may be removed and/or additional components may be added to the lobe 200. While only one lobe 200 is discussed, one skilled in the art will realize that the lobes in the plurality of lobes 113 and the plurality of lobes 114 may have the same configuration and include the same components as the lobe described in FIG. 2C.

As illustrated in FIG. 2C, the lobe 200 has a proximal end 171 and a distal end 177 and includes a top surface 172, a bottom surface 173, a ramp 174, and side surfaces 175. The ramp 174 forms a plane between the top surface 172 and the bottom surface 173. The ramp 174 can be formed at an angle relative to the top surface 172 and the bottom surface 173. The dimensions of the lobe 200 can be governed by a size of the object being crimped. In an embodiment, the width of the lobe 200 can range from approximately 25 mm to approximately 50 mm and the length of the lobe 200 can range from approximately 1 mm to approximately 40 mm. The slope ramp 174 (angle relative to the top surface 172 and the bottom surface 173) can depend on the lobes including the clamshell crimper 100. In an embodiment, the slope can be determined by dividing 360 degrees by the number of lobes 200 in the clamshell crimper 100. In an embodiment, the number of lobes 200 can range from 10 to 12. The ramp 174 is configured to contact a neighboring lobe and generate the iris effect when the lobes are displaced.

The lobe 200 also includes connection pins 176. In an embodiment, the lobe 200 can include two pairs of connection pins 176 positioned at opposing location on the side surfaces 175. The connection pins 176 operate to moveably couple the lobe 200 to the top shell 104 or the bottom shell 106. For example, when the lobe 200 is positioned between the first side 110 and the second side 112, the connection pins 176 are positioned with the connection channels of the side plates, the actuator ring 117, and the actuator ring 119. Likewise, when the lobe 200 is positioned between the first side 150 and the second side 152, the connection pins 176 are positioned with the connection channels of the side plates, the actuator ring 117, and the actuator ring 119.

In an embodiment, for example, a pair of connection pins 176 engage with the first connection channels 126 of the side plate 120 of the first side 110 and the third connection channels 136 of the top portion 116 of the actuator ring 117 (and similarly engage with opposing connection channel in the second side 112.) In this example, another pair of connection pins 176 engage with the second connection channels 126 of the side plate 120 of the first side 110 (and similarly engage with opposing connection channel in the second side 112.) Due to this connection, the rotation of the actuator ring 117 and the actuator ring 119 rotate relative to the side plates causes the lobe 200 to displace inward. When the lobe 200 is positioned to overlap the neighboring lobes 200, the displace inward causes the lobes 200 to slide along the ramps 174 thereby generating the iris effect.

In embodiments, the clamshell crimper 100 operates to convert an implantable medical device from its uncompressed state to its compressed state. Likewise, the clamshell crimper 100 operates to crimp or load the implantable medical device onto a delivery device. In operation, the implantable medical device is loaded into the bottom channel 155 and positioned in a direction that is parallel to the axis of rotation, R, of the top shell 104 and the base shell 106. The delivery device can also be positioned and aligned relative to the implantable medical device. The clamshell crimper 100 is then moved from the open state to the closed state, and the handle 102 is actuated to convert the implantable medical device from its uncompressed state to its compressed state and load the implantable medical device onto the delivery device.

To operate the clamshell crimper 100, a force can be applied to the handle 102 in the direction of the base shell 106. When the force is applied, the actuator ring 117 and the actuator ring 119 rotate in the direction that the force is applied to the handle 102. Once the actuator ring 117 and the actuator ring 119 rotate, the lobes 113 and 114 are displaced inward generating the iris effect. As such, the volume of the crimper chamber 180 decreases and the lobes 113 and 114 apply a compression force to external surfaces of the implantable medical device to crimp the expandable medical device from its uncompressed state to its compressed state. For example, if the implantable medical device is round or cylindrical in shape, the lobes 113 and 114 apply a force on the surface of the implantable medical device from various directions as force is applied to the handle 102 thereby compressing the implantable medical device.

The clamshell crimper 100 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 100 can be used with balloon-expandable medical devices, self-expandable medical devices, and/or mechanically expandable medical devices.

For example, the clamshell crimper 100 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivery through the vessels to a target location in a compressed state, and then expanded at the target location, by a balloon of the delivery device, for instance, to replace the native heart valve. By having the clamshell crimper 100 open at an angle large enough to view the bottom channel 155, a user can properly locate and position such a heart valve prosthesis with respect to the catheter. For example, when a balloon catheter with a non-crimped stent/frame of a heart valve prosthesis is placed within the clamshell crimper 100, a user can visually ensure that the prosthesis is properly located over the balloon of the catheter before proceeding with the crimping operation.

The open, top loading design of the clamshell crimper 100 provides increased visibility in loading and aligning the implantable medical devices and the delivery device as well as rapid fine adjustments. Moreover, the clamshell crimper 100 eliminates complex geometry and machining that normally defines iris crimpers.

For example, a heart valve prosthesis is typically loaded onto a delivery device or catheter at the time of the implantation procedure, e.g., at the hospital by hospital staff. The prosthesis needs to be properly aligned and loaded onto the delivery catheter because, if there is an error, the improperly aligned prosthesis may need to be discarded, which is wasteful and costly. The clamshell crimper 100 provides a straightforward and accurate procedure to crimp such a heart valve prosthesis onto a balloon catheter at the hospital.

While the components of the clamshell crimper 100 are described above with relative terms "first," "second," "proximal," and "distal," one skilled in the art will realize that the use of these terms is intended only to identify components of the clamshell crimper 100 and do not define any preferred or ordinal arrangement of the components of the crimper 100. Likewise, for example, while the implantable medical device is described as being positioned in the bottom channel 155 during operation, in an embodiment, the implantable medical device can be positioned in the top channel 115.

FIGS. 3A-3E illustrate an example of the operation of the clamshell crimper 100 in accordance with an embodiment hereof. One skilled in the art will realize that FIGS. 3A-3E illustrate one example of the operation of the clamshell crimper 100 and that existing components illustrated in FIGS. 3A-3E may be removed and/or additional components may be added to the clamshell crimper 100 without departing from the scope of the present invention. Additionally, one skilled in the art will realize that FIGS. 3A-3E illustrate only a few operating states in order to illustrate the operation of the clamshell crimper 100, and will realize that the clamshell crimper 100 can assume other operational states without departing from the scope of the present invention.

Figure 3A:
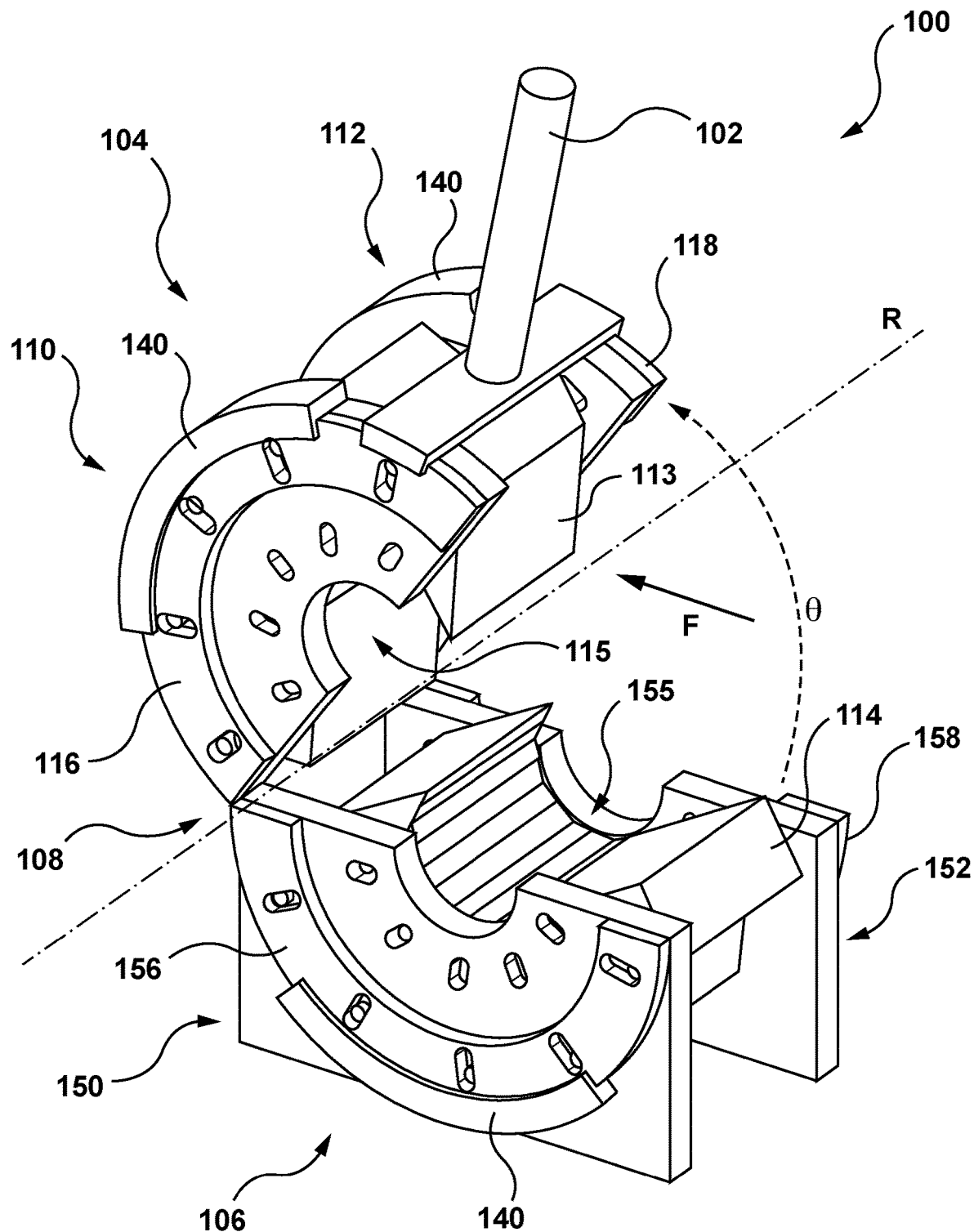
FIGS. 3A-3E depict several illustrations of the operation of the crimper of FIGS. 1A-1C, according to an embodiment hereof.

As illustrated in FIG. 3A, to load an implantable medical device, the clamshell crimper 100 can be placed to an open state by rotating the top shell 104 away from the base shell 106, about the pivot connection 108. As noted above, the open state of the clamshell crimper 100 may be any position in which the bottom channel 155 and/or top channel 115 can be viewed and accessed for inserting or placing an implantable medical device and a delivery device.

Figure 3B:
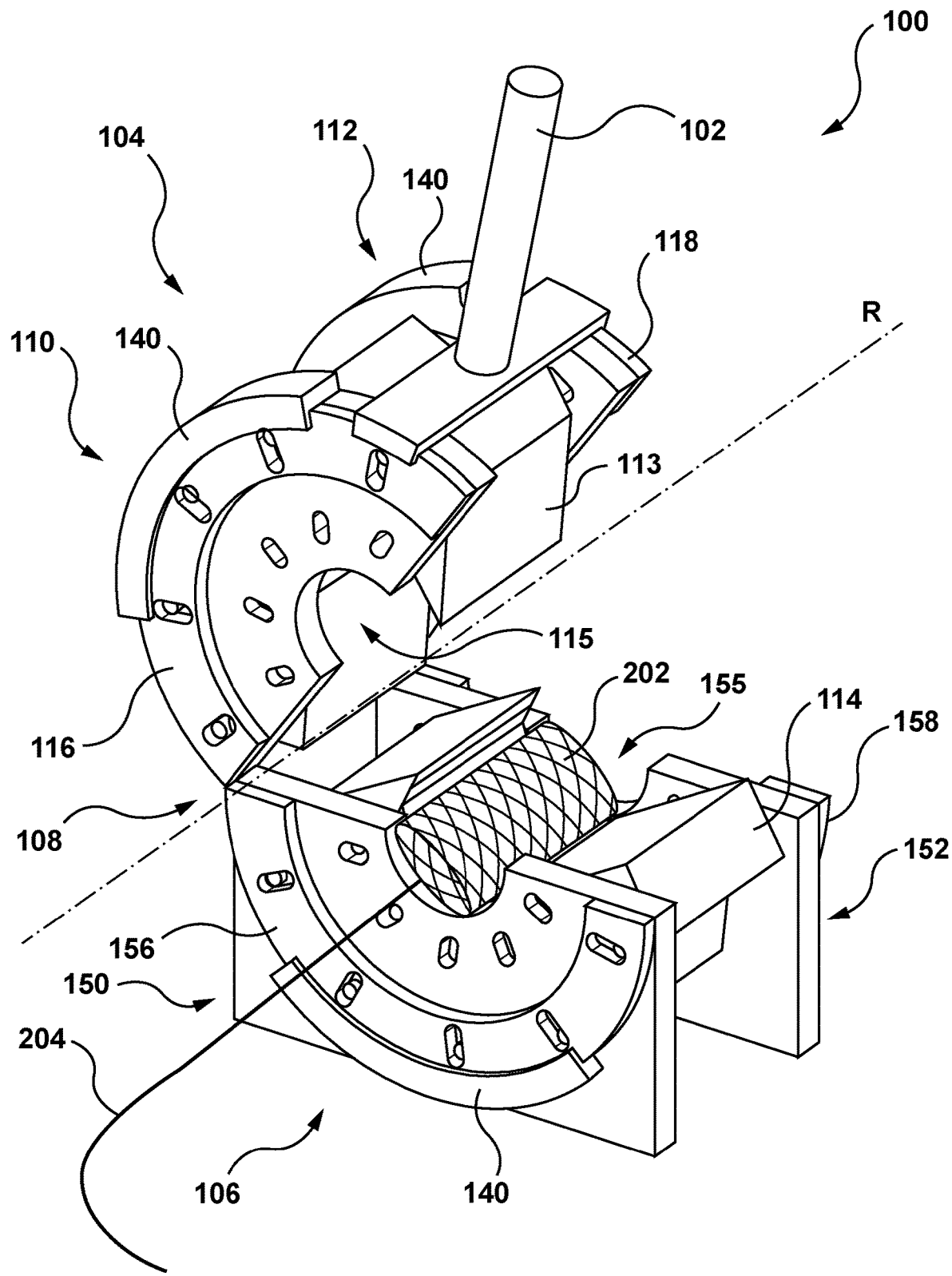

In the open state, the implantable medical device and the delivery device can be loaded into the bottom channel 155 of the base shell 106. For example, as illustrated in FIG. 3B, an implantable medical device 202 can be placed in the bottom channel 155 of the base shell 106. Likewise, a delivery device 204 can be positioned relative to the implantable medical device 202.

Figure 3C:
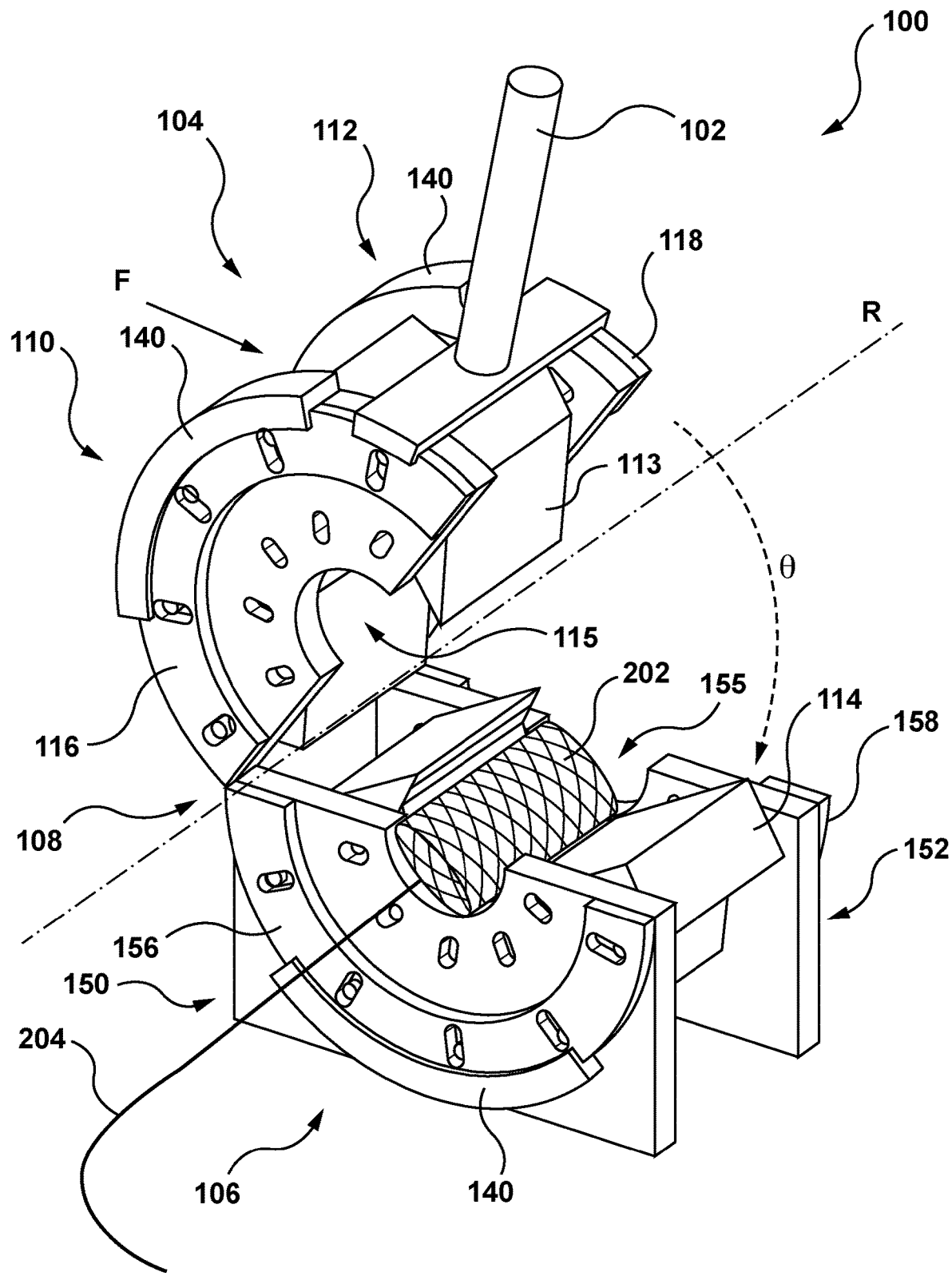
Figure 3D:
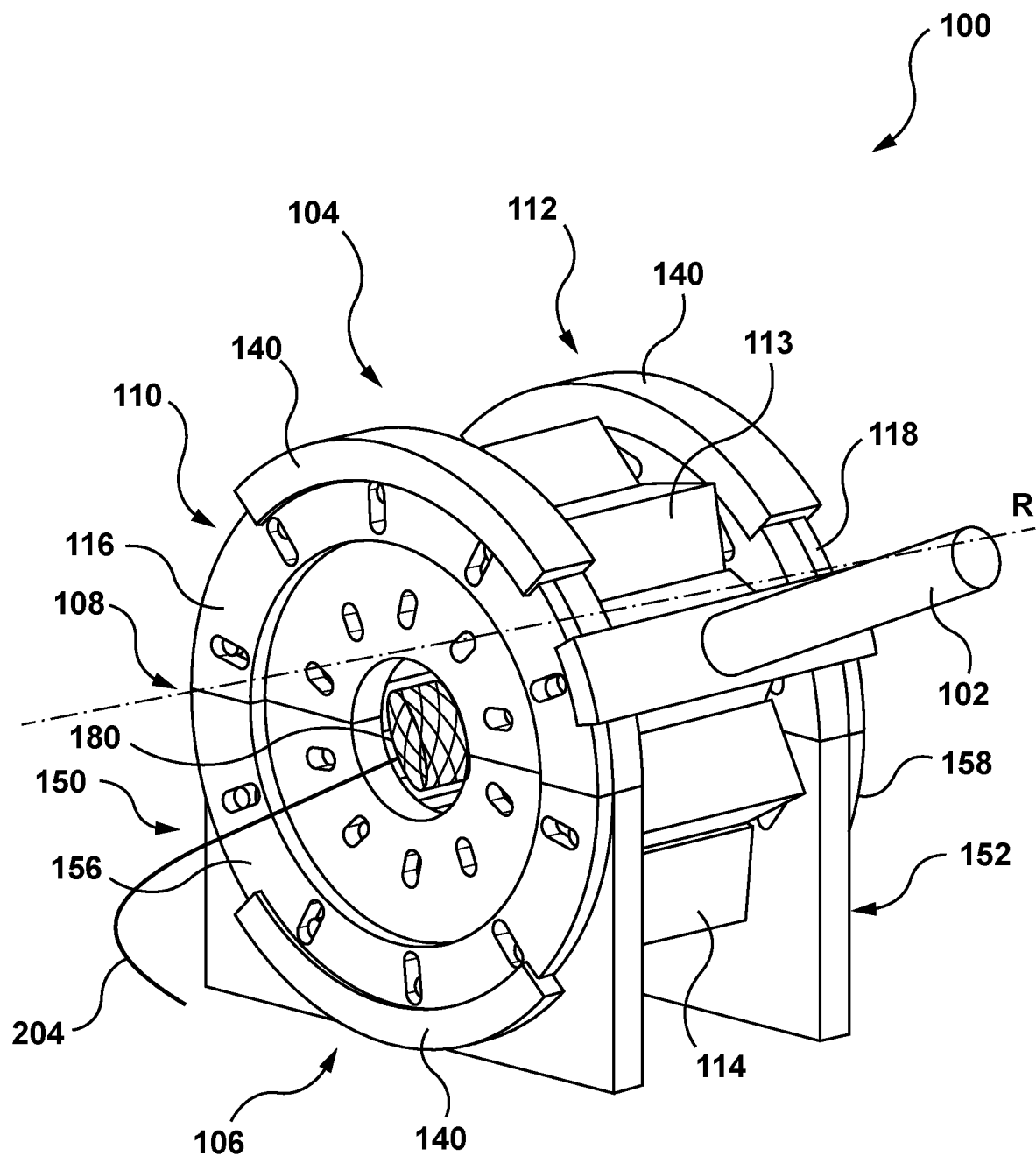

To operate the crimper 100, a force can be applied to the top shell 104. When the force is applied, the top shell 104 rotates about the pivot connection 108 towards the base shell 106, as illustrated in FIG. 3C. As the top shell 104 rotates towards the base shell 106, the clamshell crimper 100 enters the closed state. As illustrated in FIG. 3D, in the closed state, the top channel 115 formed by the plurality of the lobes 113 and the bottom channel 155 formed by the plurality of lobes 114 form the crimper chamber 180. As the volume of the crimper chamber 180 decreases, the lobes 113 and 114 apply a compression force to external surfaces of the medical device 202 to crimp alter the medical device 202 from its uncompressed state to its compressed state.

Figure 3E:
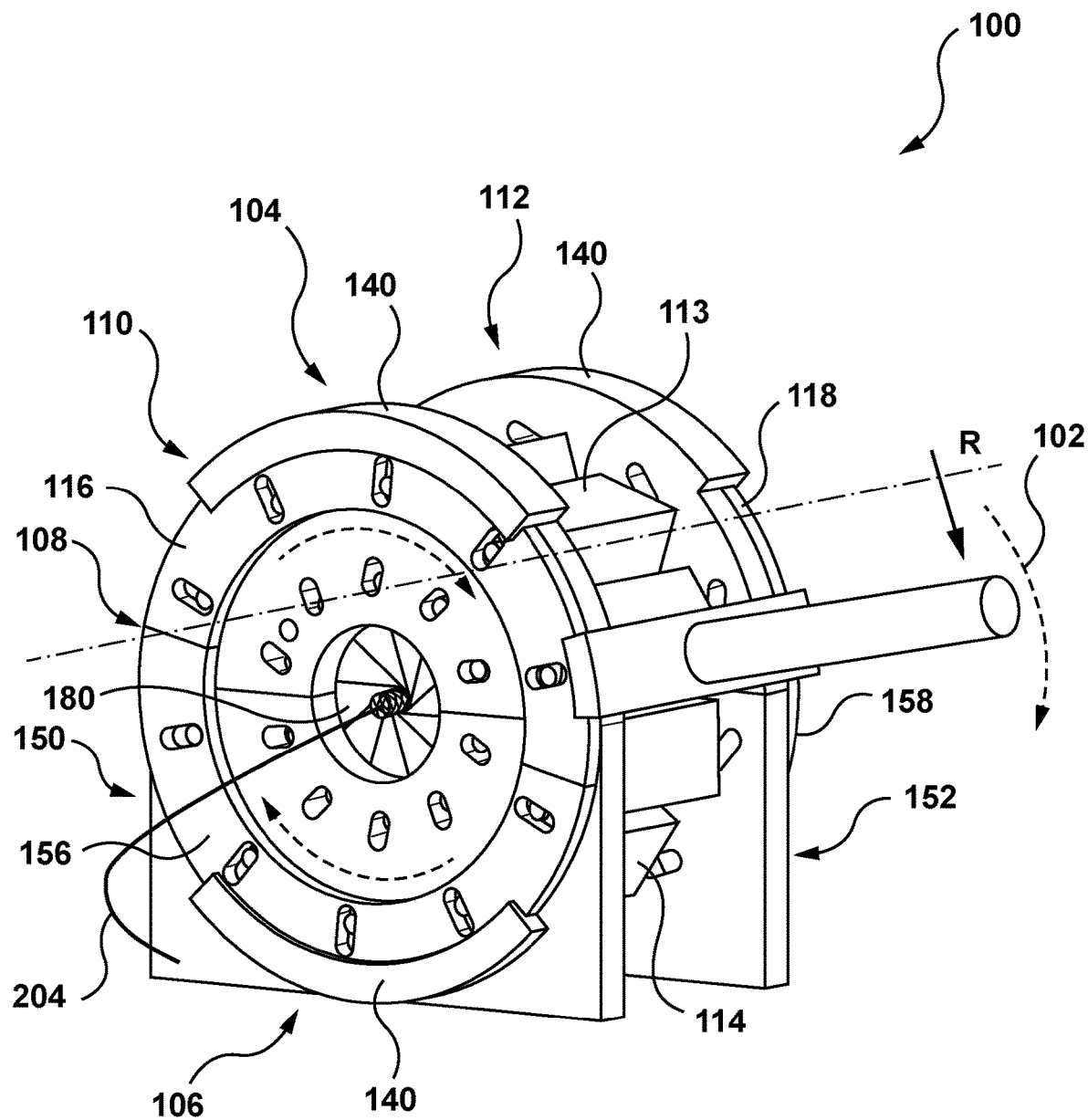

As illustrated in FIG. 3E, to compress the medical device 202, a force is applied to the handle 102 in the direction of the base shell 106. In response, the actuator ring 117 and the actuator ring 119 rotate in a clockwise direction. As the actuator ring 117 and the actuator ring 119 rotate, force is applied to the lobes 113 and 114 through the connection pins. Due to the shape of the connection channels, the lobes 113 and 114 displace inward, e.g., one lobe 113 or 114 slides along the ramp 174 of a neighboring lobe 113 or 114. As such, the displacement of the lobes 113 and 114 inward creates an iris effect thereby decreasing the volume of the crimper chamber 180.

Figure 4:
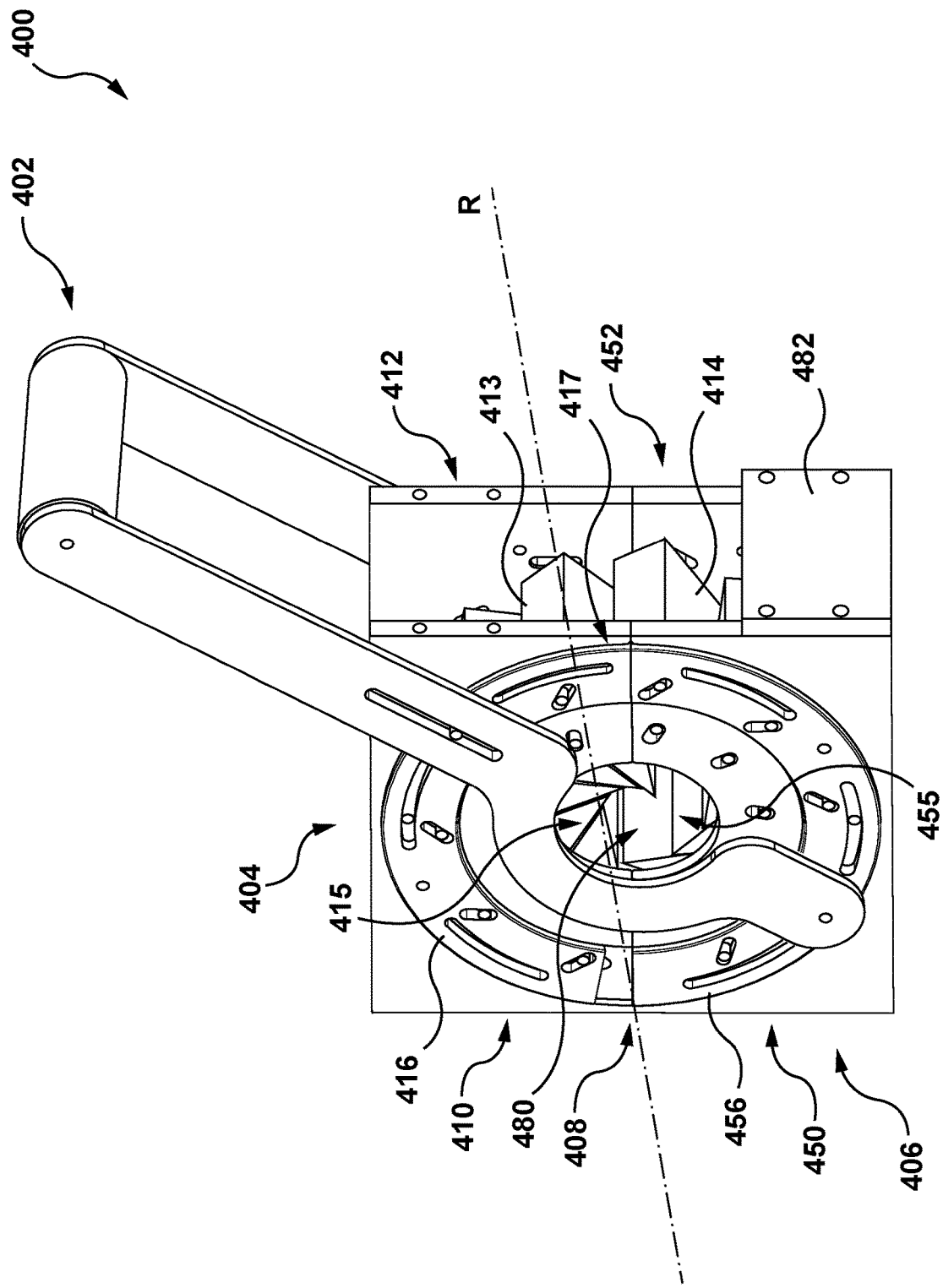
FIG. 4 depicts a perspective illustration of another clamshell crimper for use with a medical device, according to an embodiment hereof.

FIG. 4 illustrates another example of a clamshell crimper 400 in accordance with an embodiment hereof. One skilled in the art will realize that FIG. 4 illustrates one example of a crimper and that existing components illustrated in FIG. 4 may be removed and/or additional components may be added to the clamshell crimper 400.

As illustrated in FIG. 4, the clamshell crimper 400 includes a handle 402, a top shell 404 (or top iris shell), and a base shell 406 (or base iris shell). The top shell 404 and the base shell 406 are coupled at a pivot connection 408. In an embodiment, the top shell 404 and the base shell 406 can be separate components that can be removably attached at the pivot connection 408 to form the clamshell crimper 400. In another embodiment, the top shell 404 and the base shell 406 can be a single component that fold toward each other, for instance, via a living hinge therebetween, to form an integrated clamshell crimper 400. In embodiments, the handle 402 can also be removable. The top shell 404 and the base shell 406 can be formed of any suitable material such as, but not limited to aluminum, stainless steel, or a polymeric material.

Similar to the clamshell crimper 100 described in FIGS. 1A-1C, the top shell 404 and the base shell 406, when coupled, form an approximate V-shape, in which the pivot connection 408 allows an angle between the top shell 404 and the base shell 406 to be increased or decreased by rotating the top shell 404 about an axis of rotation, R. The pivot connection 108 is configured to allow the top shell 404 and the base shell 406 to move relative to each other from an open state to a closed state, as described above.

The pivot connection 408 can be any type of mechanical joint or electro-mechanical joint that allows the top shell 404 and the base shell 406 to move relative to each other. For example, the pivot connection 408 can include one or more of a hinge, a rivet, a pivot pin, a pivot joint, an axel, a living hinge, etc. In an embodiment, the pivot connection 408 can include a movement assistance device to provide a force that assists in the movement of the top shell 404 and the base shell 406 relative to each other. For example, the pivot connection 408 can include a spring, a motor, etc. In some embodiments, the top shell 404 and the bottom shell 406 can include tabs that extend from back of the top shell 404 and the bottom shell 406. The tabs, when mated, can form a concentric hole that operates as the pivot connection 408 when pin, rivet, bolt, screw or other connecting mechanism.

In embodiments, the top shell 404 can include a lock mechanism that locks the handle 402 into an open position, e.g., the crimper chamber 480 in an open position. The top shell 404 and/or the bottom shell 406 can include a locking mechanism that locks the top shell 404 and the bottom shell 406 together in a closed state. When the handle 402 is locked, the clamshell crimper 400 can be moved into an open state by pivoting the top shell 404 away from the bottom shell 406. During crimping operations, the top shell 404 can be closed, for example, using the handle 402, and the top shell 404 and the bottom shell 406 can be locked into the closed state. The handle 402 can then be unlocked to perform crimping operations. The dual locking can prevent either the top shell 404 or the bottom shell 406 from moving to the closed position while the other half is in the open position.

In embodiments, the handle 402 can be shape, size, design, and/or configuration to accommodate different crimping operations. For example, the handle 402 can be extended and include a pivot point to add more leverage during crimping operations. Likewise, the handle 402 can include a foot pedal that assists in pulling down the handle 402.

The top shell 404 includes a first side 410 and a second side 412. A plurality of lobes 413 are coupled between the first side 410 and the second side 412. The plurality of lobes 413 are positioned within the top shell 404 to define a top channel 415. The first side 410 of the top shell 404 also includes a top portion 416 of an actuator ring 417. While not shown, the second side 412 of the top shell 404 also includes components that mirror the first side 410. In embodiments, the lobes 413 can be configured as described in FIG. 2C.

The base shell 406 includes a first side 450 and a second side 452 coupled by a brace 482. A plurality of lobes 414 are coupled between the first side 450 and the second side 452. The plurality of lobes 414 are positioned within the base shell 406 to define a bottom channel 455. The first side 450 of the base shell 406 also includes a bottom portion 456 of the actuator ring 417. While not shown, the second side 452 of the bottom shell 406 also includes components that mirror the first side 450. In embodiments, the lobes 414 can be configured as described in FIG. 2C.

As discussed above for FIGS. 1A-1C, the plurality of lobes 413 and 414 are arranged to partially overlap between the top shell 404 and the base shell 406, respectively, in a first direction. In an embodiment, the lobes 413 are arranged to partially overlap to form the top channel 415 at distal ends of the lobes 413. The lobes 413 are arranged to partially overlap to form the bottom channel 455 at distal ends of the lobes 413. When the clamshell crimper 400 is in the closed state, the top channel 415 and the bottom channel 455 define a crimper chamber 480. That is, when in the closed state, the lobes 413 and 414 form a cylinder of overlapping lobes with a cylindrical-shaped cavity passing through the center, the crimper chamber 480. The handle 402 is coupled the actuator ring 417 of the first sides of the second sides of the top shell 404 and the base shell 406, and the actuator ring (not shown) of the second sides of the top shell 404 and the base shell 406 as further described below in reference to FIG. 7.

The clamshell crimper 400 is configured to receive an implantable medical device and alter the implantable medical device from an uncompressed state to a compressed state by the displacement of the lobes 413 and 414, which causes the decrease of the volume of the crimper chamber 480, as described above in detail. Additionally, the clamshell crimper 400 is configured to crimp or load the implantable medical device onto a delivery device. In an embodiment, the lobes 413 and 414 can be removable from the top shell 404 and/or base shell 406. As such, the lobes 413 and 414 may be interchangeable with other types of lobes configured to accommodate different dimensions and/or configurations of implantable medical devices and/or delivery devices. The lobes 413 and 414 may be formed of any suitable material such as, but not limited to aluminum, stainless steel, or a polymeric material.

Figure 5:
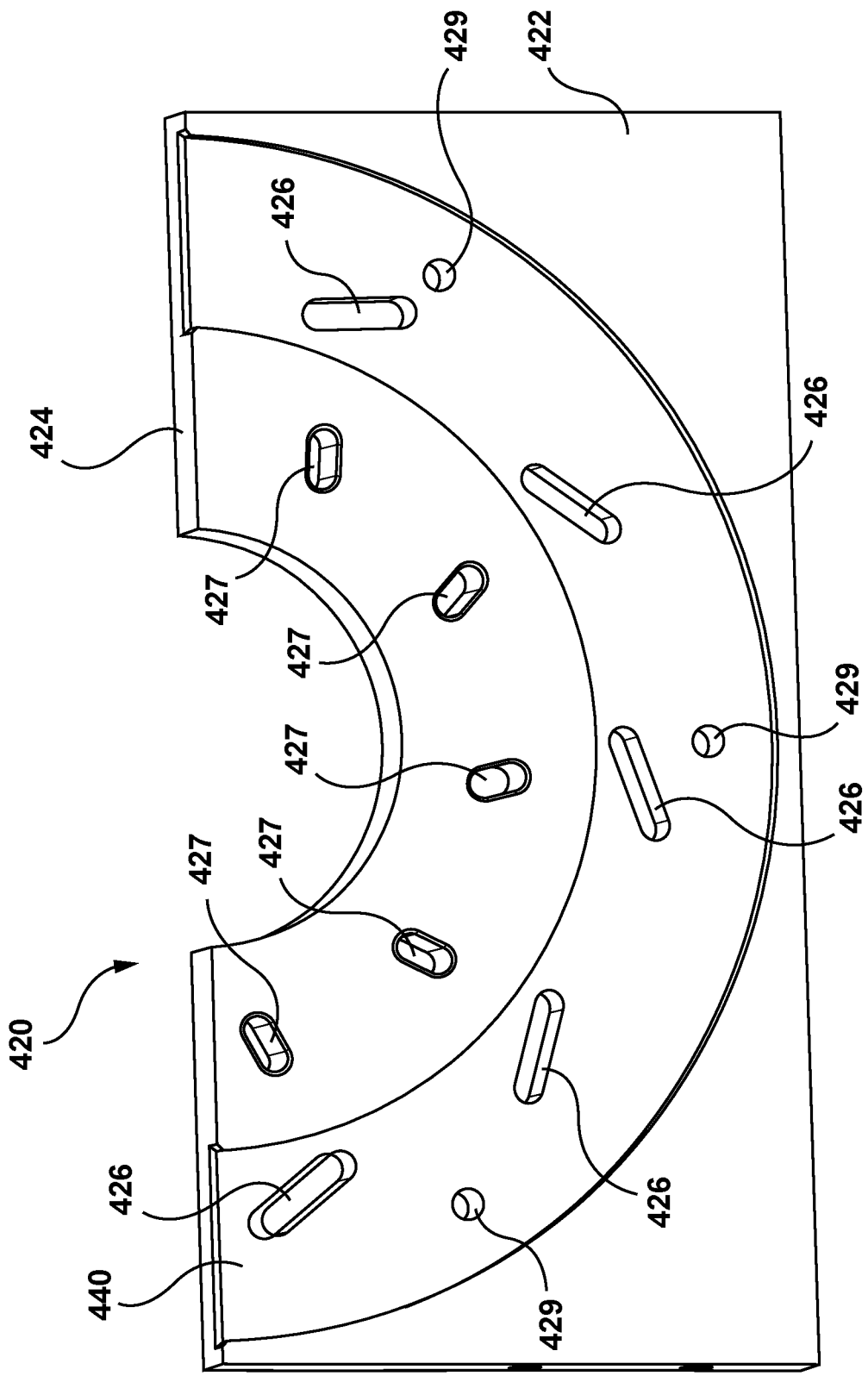
FIG. 5 depicts a perspective illustration of a side wall of the crimper of FIG. 4, according to an embodiment hereof.

FIG. 5 illustrates a detailed view of components of a side plate 420 which may be used in the clamshell crimper 400. One skilled in the art will realize that FIG. 5 illustrates one example of a side plate and that existing components illustrated in FIG. 5 may be removed and/or additional components may be added to the side plate 420. Additionally, one skilled in the art will realize that the side plate may be used in any of the sides of the top shell 404 or base shell 406.

As illustrated in FIG. 5, the side plate 420 with a front surface 422 and a back surface 424. In an embodiment, the side plate 420 can be constructed as a plate with a semi-cylindrical opening 425. The semi-cylindrical opening 425 allows access to the top channel 415 (or the bottom channel 455) formed by the plurality of lobes 413 (or the plurality of lobes 414). First connection channels 426 are formed through the side plate 420 from the front surface 422 to the back surface 424. The first connection channels 426 can be positioned in an arc, at equal distances, along an outer edge of the side plate 420. Second connection channels 427 are formed through the side plate 420 from the front surface 422 to the back surface 424. The second connection channels 427 can be positioned in an arc, at equal distances, along an inner edge of the side plate 420 around the opening 425.

Auxiliary holes 429 are formed through the side pate 420 from the front surface 432 to the back surface 434. The auxiliary holes 429 can be interspaced between the first connection channels 426. In embodiments, the auxiliary holes 429 can be threaded holes that correspond to a slot in actuation rings, e.g., the actuator rings on both sides of clamshell crimper 400, which operates to hold the actuator ring in place. In embodiments, as a lobe 413 pivots in channel 427, the first connection channel 426 can operate as a guide that forces the lobe 413, when circumferential pressure is applied, from a position sitting along the diameter to a more radial position, thereby lowering the diameter of the crimper chamber 480 and circumferentially crimping an implantable medical device placed in the crimper chamber 480.

Figure 6:
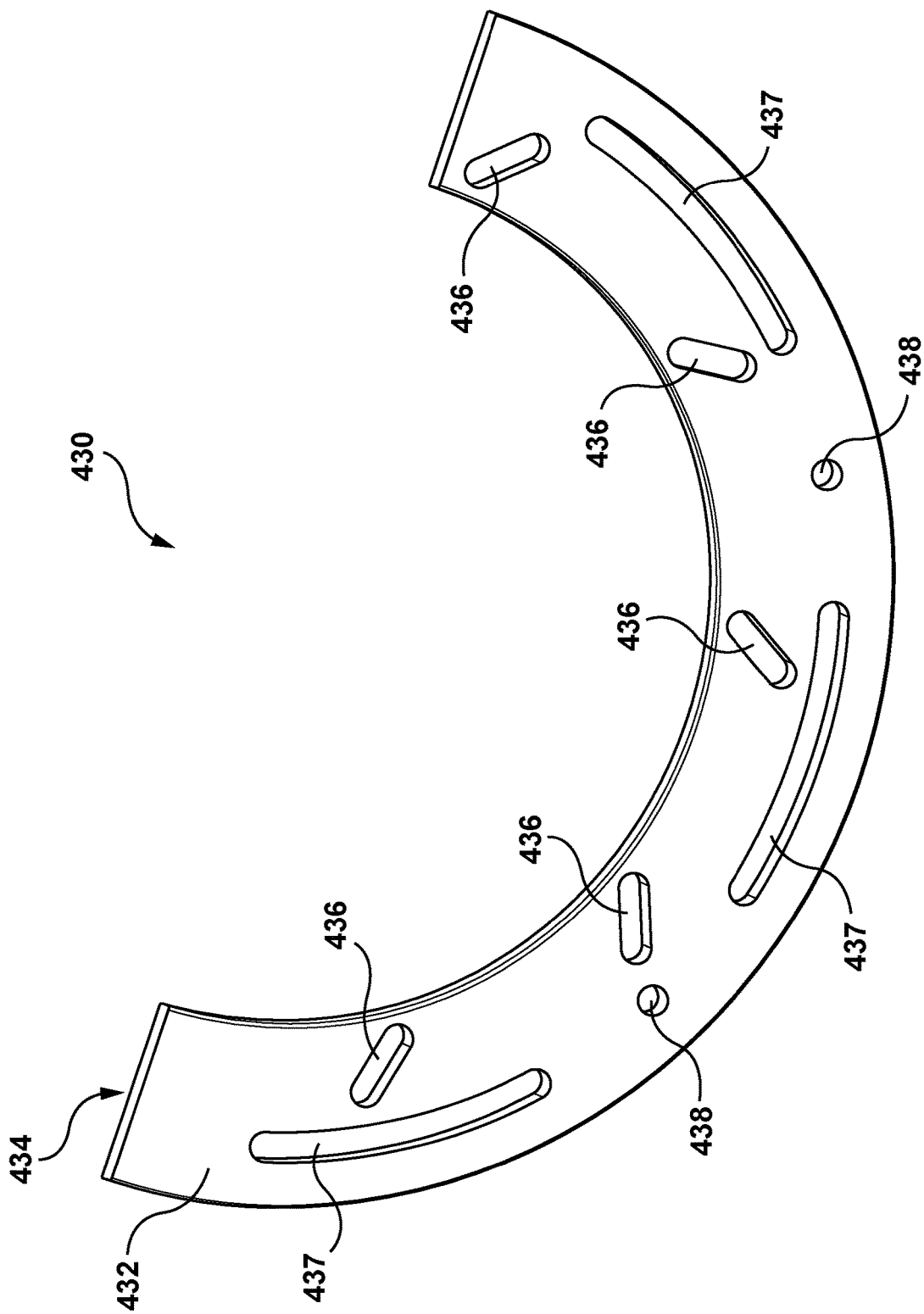
FIG. 6 depicts a perspective illustration of a portion of an actuator ring of the crimper of FIG. 4, according to an embodiment hereof.

FIG. 6 illustrates a detailed view of components of a portion 430 of an actuator ring which may be used in the clamshell crimper 400. One skilled in the art will realize that FIG. 6 illustrates one example of a portion of the actuator ring and that existing components illustrated in FIG. 6 may be removed and/or additional components may be added to the portion 430 of an actuator ring. Additionally, one skilled in the art will realize that the portion 430 of the actuator ring may be used as any of the portions of the actuator rings, e.g., the actuator rings on both sides of the clamshell crimper 400.

As illustrated in FIG. 6, the portion 430 of the actuator ring includes a front surface 432 and a back surface 434. The portion 430 can be constructed as a semi-cylindrical donut. When in combination two copies of the portion 430 can form, in a cylindrical donut shape, the actuator ring 417 of the first sides of the second sides of the top shell 404 and the base shell 406, and the actuator ring (not shown) of the second sides of the top shell 404 and the base shell 406. Third connection channels 436 are formed through the portion 430 from the front surface 432 to the back surface 434. The third connection channels 436 can be positioned in an arc, at equal distances, along an inner edge of the portion 430 of the actuator. Connection channels 437 are formed through the portion 430 from the front surface 432 to the back surface 434. The connection channels 437 can be positioned in an arc, at equal distances, along an outer edge of the portion 430 of the actuator.

Auxiliary holes 438 are formed through the portion 430 from the front surface 432 to the back surface 434. The auxiliary holes 438 can be interspaced between the connection channels 437. In embodiments, screws, bolts, pins, etc. can be inserted through the connection channels 437 and couple to the auxiliary holes 429. The auxiliary holes 438 can operate as connection points for the handle 402. In embodiments, the actuator ring can include several auxiliary holes 438 positioned at different locations on the actuator ring to accommodate different connection points for the handle 402. The handle 402 can be connected to one of the auxiliary holes 438. The different locations of the auxiliary holes 438 can be utilized to accommodate different handle sizes and configurations and to accommodate different crimping diameters of the crimper chamber 480.

Figure 7:
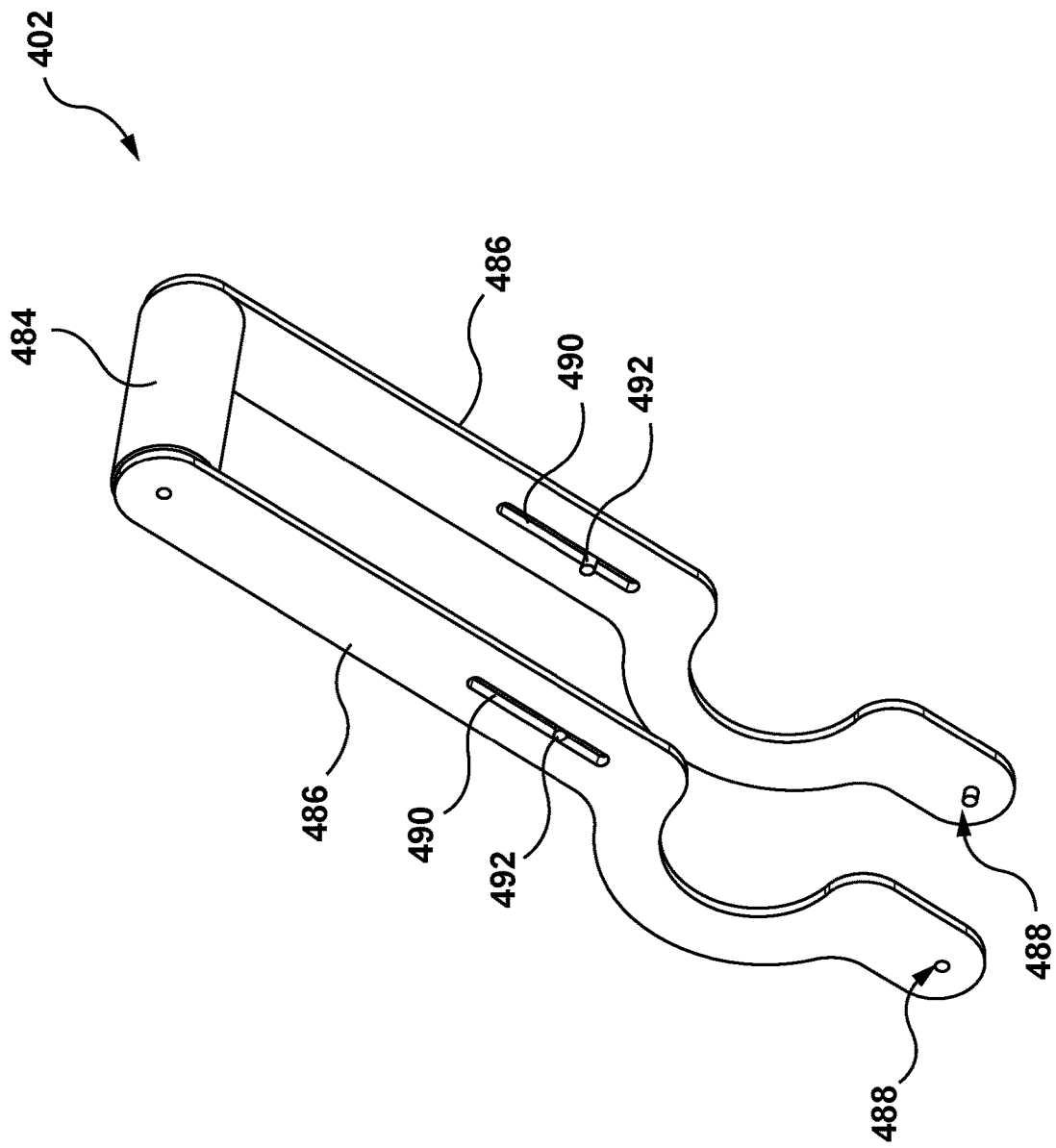
FIG. 7 depicts a perspective illustration of a handle of the crimper of FIG. 4, according to an embodiment hereof.

FIG. 7 illustrates a detailed view of components of the handle 402 which may be used in the clamshell crimper 400. One skilled in the art will realize that FIG. 7 illustrates one example of a handle and that existing components illustrated in FIG. 6 may be removed and/or additional components may be added to the handle 402.

As illustrated in FIG. 7, the handle 402 includes a handle bar 484 coupled between two handle arms 486 at a proximal end of the handle arms 486. The handle 402 also includes first connection pins 488 coupled to a distal end of the handle arms 486. The handle also includes handle connection channels 490 formed in the handle arms 486 between the proximal and distal ends of the handle arms 486. The handle connection channels 490 are configured to receive second connection pins 492.

As illustrated in FIG. 4, the first connection pins 488 can be positioned to engage the connection channel 437 of the portions of the actuator rings located in the base shell 406. The second connection pin 492 can be positioned to engage the connection channel 437 of the portions of the actuator rings located in the top shell 404. In operation, when a force is applied to the handle 402, lever action caused by the two connection points cause the actuator rings to rotate. To allow the handle 102 to move freely, the second connection pins 492 may slide in the channels 490 as the handle 102 is actuated.

In operation, as similarly described above, in an embodiment, for example, a pair of connection pins of a lobe 413 or 414 (e.g., connector pins 176 described above with reference to FIG. 2C) engage with the first connection channels 426 of the side plate 420 of the first side 410 and the third connection channels 436 of the portion 420 of the actuator ring (and similarly engage with opposing connection channel in the second side 412.) In this example, another pair of connection pins (e.g., connector pins 176 described above with reference to FIG. 2C) engage with the second connection channels 426 of the side plate 420 of the first side 410 (and similarly engage with opposing connection channel in the second side 412.) Due to this connection, the rotation of the actuator rings rotate relative to the side plates causes the lobe 413 or 414 to displace inward. When the lobe 413 or 414 positioned to overlap the neighboring lobes 413 or 414, the displacement inward causes the lobes 413 and 414 to slide along the ramps 174 thereby generating the iris effect.

While the components of the clamshell crimper 400 are described above with relative terms "first," "second," "proximal," and "distal," one skilled in the art will realize that the use of these terms is intended only to identify components of the clamshell crimper 400 and do not define any preferred or ordinal arrangement of the components of the crimper 400. Likewise, for example, while the implantable medical device is described as being positioned in the bottom channel 455 during operation, in an embodiment, the implantable medical device can be positioned in the top channel 115.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A clamshell crimper for altering an expandable medical device from an uncompressed state to a compressed state, the crimper comprising:
   a top shell comprising a first plurality of lobes, the first plurality of lobes defining a top channel;
   a base shell comprising a second plurality of lobes, the second plurality of lobes defining a bottom channel, wherein:
     the top shell and the base shell are coupled at a pivot connection,
     the top shell is configured to rotate about the pivot connection relative to the base shell from an open state to a closed state,
     when in the open state, the bottom channel is exposed for loading the expandable medical device, and
     when in the closed state, the top channel and the bottom channel define a crimper chamber;
   a handle configured to operate the clamshell crimper; and
   one or more actuator rings coupled to the handle, the first plurality of lobes, and the second plurality of lobes, wherein:
     when in the closed state, movement of the handle rotates the one or more actuator rings thereby displacing the first plurality of lobes and the second plurality of lobes, and
     the displacement of the first plurality of lobes and the second plurality of lobes decreases a volume of the crimper chamber to transition the expandable medical device from the uncompressed state to the compressed state.

2. The clamshell crimper of claim 1, wherein the top shell or the base shell comprises a first side and a second side, wherein the first plurality of lobes is movably coupled between the first side and the second side.

3. The clamshell crimper of claim 2, wherein one of the first side or the second side comprises:
   a side plate comprising a front surface and a back surface, wherein:
     a plurality of first connection channels are formed through the side plate from the front surface and the back surface, and
     a plurality of second connection channels are formed through the side plate from the front surface and a back surface.

4. The clamshell crimper of claim 3, wherein one of the first side or the second side further comprises:
   a retention member coupled to the side plate; and
   a portion of the one or more actuator rings configured to be movably positioned within the retention member, the portion of the one or more actuator rings comprising a front surface and a back surface, wherein:
     a plurality of third connection channels are formed through the portion of the one or more actuator rings from the front surface and the back surface, and when in the open state, the portion of the one or more actuator rings separates from another portion of the one or more actuator rings.

5. The clamshell crimper of claim 4, wherein a lobe from the first plurality of lobes or the second plurality of lobes comprises a plurality of connection pins,
wherein the first connection pin is positioned within one of the plurality of first connection channels,
wherein, for each of the first plurality of lobes, the second connection pin is positioned with one of plurality of second connection channels and one of the plurality of third connection channels, and
wherein the movement of the handle displaces the portion of the one or more actuator rings thereby causing the displacement of the first plurality of lobes.

6. The clamshell crimper of claim 2, wherein one of the first side or the second side comprises:
a side plate comprising a front surface and a back surface, wherein:
a semi-circular actuator ring channel is formed within the front surface,
a plurality of first connection channels are formed through the side plate from the front surface and the back surface, and
a plurality of second connection channels are formed through the side plate from the front surface and a back surface within the semi-circular actuator ring channel.

7. The clamshell crimper of claim 6, wherein one of the first side or the second side further comprises:
a portion of the one or more actuator rings positioned within the semi-circular actuator ring channel, the portion of the actuator ring comprising a front surface and a back surface, wherein:
a plurality of third connection channels are formed through the portion of the one or more actuator rings from the front surface and the back surface, and
when in the open state, the portion of the one or more actuator rings separates from another portion of the one or more actuator rings.

8. The clamshell crimper of claim 7, wherein a lobe from the first plurality of lobes or the second plurality of lobes comprises a plurality of connection pins,
wherein the first connection pin is positioned within one of the plurality of first connection channels,
wherein, for each of the first plurality of lobes, the second connection pin is positioned with one of plurality of second connection channels and one of the plurality of third connection channels, and
wherein the movement of the handle displaces the portion of the one or more actuator rings thereby causing the displacement of the first plurality of lobes.

9. The clamshell crimper of claim 8, wherein the handle comprises:
a first arm and a second arm;
a handle bar coupled between the first arm and second arm at proximal ends of the first arm and the second arm;
first connection pins positioned at distal ends of the first arm and the second arm; and
first handle connection channels formed within the first arm and the second arm.

10. The clamshell crimper of claim 9, wherein a plurality of second handle connection channels are formed through the portion of the one or more actuator rings from the front surface and the back surface,
wherein the first arm and the second arm are coupled to the portion of the one or more actuator rings by second connection pins positioned in the first handle connection channels and second handle connection channels from the plurality of handle connection channels, and
wherein the first arm and the second arm are coupled to another portion of the one or more actuator rings by first connection pins being positioned in second handle connection channels formed in the another portion of the one or more actuator rings.

11. The clamshell crimper of claim 2, wherein each lobe from the plurality of lobes comprises a slanted side wall for contact with an adjacent lobe from the plurality of lobes.

12. The clamshell crimper of claim 2, wherein the first side and the second side of the base shell comprise one or more base surfaces for supporting the clamshell crimper.

13. The clamshell crimper of claim 1, wherein the top shell further comprises a first locking mechanism, wherein the first locking mechanism locks the handle into an open position to enable movement of the top shell from the closed state to the open state.

14. The clamshell crimper of claim 13, wherein at least one of the top shell or the base shell further comprises a second locking mechanism, wherein the second locking mechanism locks the top shell and the base shell into the closed state.

15. A clamshell crimper for altering an expandable medical device from an uncompressed state to a compressed state, the crimper comprising:
a top iris shell defining a top iris channel;
a base iris shell coupled to the top iris shell at a pivot connection, the base iris shell defining a base iris channel, wherein:
the top iris shell is configured to rotate about the pivot connection relative to the base shell from an open state to a closed state,
when in the open state, the base iris channel is exposed for loading the expandable medical device, and
when in the closed state, the top iris channel and the base iris channel define a crimper chamber; and
a handle configured to operate the clamshell crimper, wherein the actuation of the handle decreases a volume of the crimper chamber to transition the expandable medical device from the uncompressed state to the compressed state, and
wherein the top iris shell comprises a first portion of a first actuator ring, a first portion of a second actuator ring, and a first plurality of lobes moveably coupled between the first portion of the first actuator ring and the first portion of the second actuator ring, wherein the first plurality of lobes defines the top iris channel.

16. The clamshell crimper of claim 15, wherein the base iris shell comprises:
a second portion of the first actuator ring;
a second portion of the second actuator ring; and
a second plurality of lobes moveably coupled between the second portion of the first actuator ring and the second portion of the second actuator ring, wherein the second plurality of lobes defines the base iris channel.

17. The clamshell crimper of claim 16, wherein, when in an open state, the first portion of the first actuator ring is separated from the second portion of the first actuator ring and the first portion of the second actuator ring is separated from a second portion of the second actuator ring.

18. The clamshell crimper of claim 16, wherein the handle is coupled to one or more of the first portion of the first actuator ring, the first portion of the second actuator ring, a second portion of the first actuator ring, and a second portion of the second actuator ring, wherein actuation of the handle causes rotation of the first actuator ring and the second actuator ring thereby causing displacement of the first plurality of lobes and the second plurality of lobes, and wherein the displacement of the first plurality of lobes and the second plurality of lobes causes the decrease in volume of the crimper chamber.

\* \* \* \* \*